United States Patent [19]

Baldwin et al.

[11] Patent Number: 5,017,560
[45] Date of Patent: May 21, 1991

[54] POULTRY GROWTH PROMOTION

[75] Inventors: Chauncey D. Baldwin; Brian R. Shricker; Richard E. Ivy, all of Terre Haute, Ind.

[73] Assignee: Pitman-Moore, Inc., Lake Forest, Ill.

[21] Appl. No.: 117,303

[22] Filed: Nov. 6, 1987

[51] Int. Cl.$^5$ .................... A61K 9/08; A61K 35/55; A61K 37/02
[52] U.S. Cl. .................... 514/21; 424/499; 424/486; 424/80; 424/565; 424/423; 424/425; 426/807
[58] Field of Search .................... 514/21; 424/499, 486, 424/80, 108, 423, 425; 426/807

[56] References Cited

U.S. PATENT DOCUMENTS

| | | | |
|---|---|---|---|
| 3,265,580 | 8/1966 | Nelson | 167/74 |
| 3,275,516 | 9/1966 | Eppstein | 167/74 |
| 3,317,392 | 5/1967 | Eppstein | 167/74 |
| 4,525,938 | 7/1985 | Churchill | 525/415 |
| 4,639,435 | 1/1987 | Fujii et al. | 514/11 |
| 4,666,839 | 5/1987 | Souza | 435/91 |
| 4,675,297 | 6/1987 | Baxter et al. | 435/253 |
| 4,725,549 | 2/1988 | Cooke et al. | 435/243 |

OTHER PUBLICATIONS

The Merck Index, 9th ed., Merck and Co., Inc., 1976, Entry No. 7498.
Doneen et al., *Biochem*, 18, 4851–4860, (1979), Discloses Studies on Prolactin.
Lewis et al., *Biochem and Biophysical Research Communications*, vol. 44, No. 5, (1971), Discloses the Isolation and Some Properties of Human Prolactin.
West et al., *Textbook of Biochemistry*, 4th ed., the MacMillan Co., N.Y., U.S.A., 1966, p. 325

Primary Examiner—Ronald W. Griffin
Attorney, Agent, or Firm—Wendell Ray Guffey; Thomas L. Farquer

[57] ABSTRACT

Porcine prolactin (pPRL) is administered to poultry in dosages of from about 1–500 ug/kg/day, preferably 10–100 ug/kg/day, to promote growth by improving the rate of weight gain and/or increasing feed utilization efficiency.

11 Claims, 1 Drawing Sheet

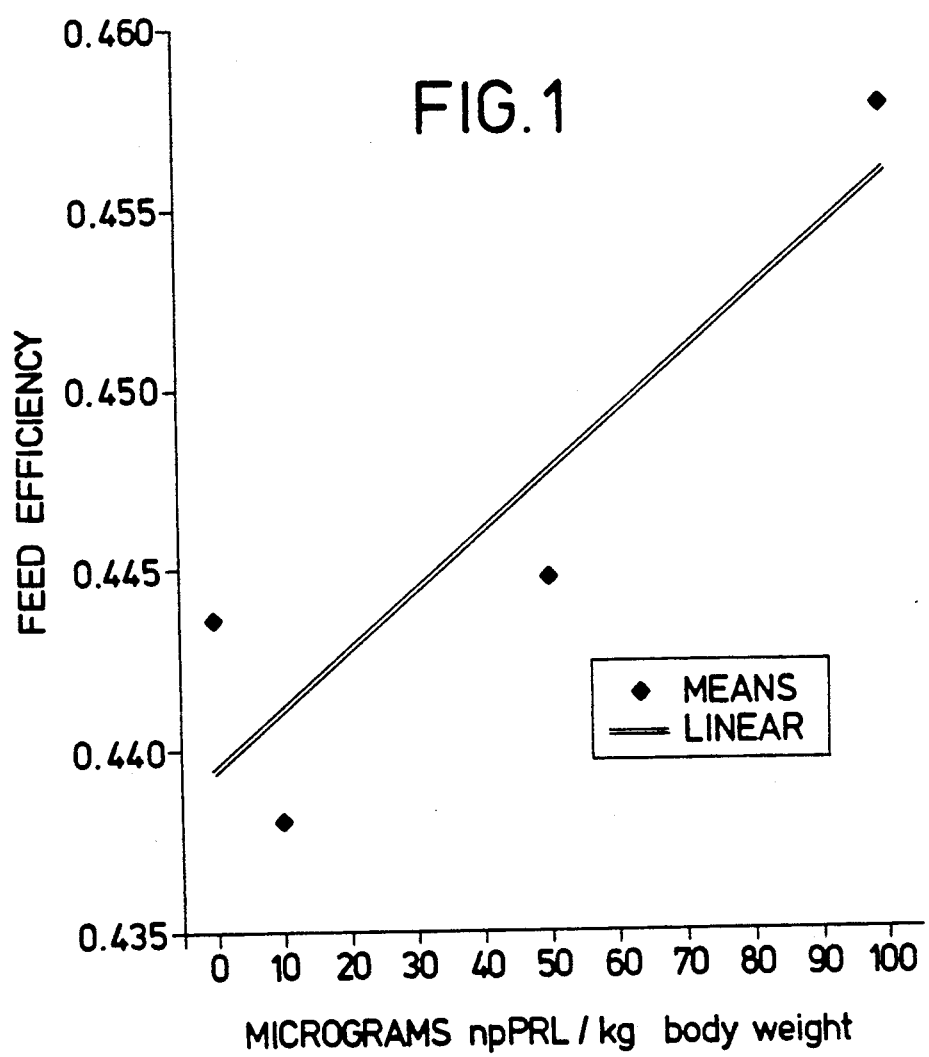

POULTRY GROWTH PROMOTION

This invention relates generally to methods for promoting growth in poultry and particularly to a method for using porcine prolactin to promote growth in poultry.

BACKGROUND OF THE INVENTION

Generally, prolactin (PRL) is a 199 amino acid protein which is normally produced by the pituitary throughout an animal's life. PRL plays a role in the development of mammary tissue in females and, during pregnancy, produces a further development of mammary tissue and stimulates the production of milk. Although known for its mammatropic and lactogenic effects, PRL is generally not considered an efficient anabolic agent. In addition, PRL is considered species specific. Human, ovine, and porcine PRL have 144 of their 199 residues in identical positions but neither the ovine nor porcine PRL is active in humans.

PRL has been isolated from excised pituitary tissue. See, e.g., Li et al., *Nature*, 224, 695-696 (1963) (ovine); Lewis et al., *Biochem Biophys. Res. Commun.*, 44(5), 1169 (1971) (human); Reisfeld et al., *J. Am. Chem. Soc.*, 83, 3719 (1961) (sheep); and Li et al., *J. Biol Chem*, 146, 627 (1942) (ox, sheep and swine) PRL can also be obtained from genetically engineered microorganisms containing recombinant DNA which specifies the production of PRL using well known techniques. For example, the nucleotide coding sequence and an amino acid sequence of native bovine prolactin (bPRL) have been reported; e.g. W.L. Miller et al., *J. Biol. Chem.*, 255, 7521-24 (1980); U.S. Pat. No. 4,666,839 to Souza discloses a method for preparing bPRL by utilizing recombinant DNA methodology.

The preparation of porcine prolactin (pPRL) is well known in the art. For example, pPRL is extracted from pituitary glands of swine or can be produced via recombinant DNA technology in appropriate hosts by means well known to skilled artisans. U.S. Pat. Nos. 3,317,392 to Eppstein and 3,265,580 to Nelson et al, both incorporated by reference herein, disclose processes for preparing porcine prolactin from porcine pituitary glands. PRL can be purchased commercially from Pituitary Hormones and Antisera Center, Harbour/U.C.L.A. Medical Center, 1000 West Carson Street, Torrance, CA.

FRL produced in animals of different species vary in antigens induced, isoelectric points, N-terminal and C-terminal amino acid residues, and amino acid composition. PRL is generally species-specific that is PRL from one species is inactive or has very weak activity in another species.

This species specific limitation on the use of PRL has several disadvantages. Equipment, expertise, recombinant microorganism strains, process and handling conditions, etc. must be obtained or developed for the production of PRL for each desired species. Additionally, PRL for one species may be more costly to produce, more difficult to recover, or less stable than PRL for a different species. It would, therefore, save considerable expense and duplication of effort if, contrary to previous teachings, the PRL from one species could be used to treat other non-related species. For example, a particular advantage in costs and duplication of effort could be saved if PRL from one species could be used to promote growth in another species. Such a surprising discovery would be contrary to two prior previous teachings relating to PRL; (1) that PRL is species specific, and (2) that PRL is not an effective anabolic agent.

SUMMARY OF THE INVENTION

It is, therefore, an object of the present invention to provide a method for promoting growth in one species using prolactin from another species.

It is another object of the present invention to provide a method for promoting growth in poultry using porcine prolactin.

It is another object of the present invention to provide a method for increasing weight gain in poultry using porcine prolactin.

It is a further object of the present invention to provide a method for increasing feed utilization efficiency in poultry using porcine prolactin.

These and other objects are achieved by administering porcine prolactin (pPRL) to poultry in amounts sufficient to promote growth by improving the rate of weight gain and increasing feed utilization efficiency.

In the preferred embodiment, pPRL is administered to poultry in dosages from about 1-500 micrograms/kilogram body weight/day (ug/kg/day), preferably 10-100 ug/kg/day, to promote growth.

Other objects, advantages, and novel features of the present invention will become apparent from the following detailed description of the invention.

DESCRIPTION OF DRAWINGS

FIG. 1 is a graph showing the effect of daily injections of native porcine prolactin on feed efficiency of male broilers when treated according to the present invention.

DETAILED DESCRIPTION OF THE INVENTION

According to the present invention porcine prolactin (pPRL) is administered to poultry in amounts sufficient to promote growth. The term "promote growth" is defined herein to mean improving the rate of weight gain and/or increasing feed utilization efficiency for poultry.

PRL can be obtained from any suitable source. Methods for producing, isolating and purifying native and recombinant pPRL are well known in the field. pPRL as used herein includes all proteins having pPRL activity including natural, recombinant, and mutein proteins having deleted, replaced, or altered amino acid sequences.

Although the dosages of pPRL vary according to the age, size, and character of the particular bird, pPRL is typically administered to the bird in dosages from about 1-500 ug/kg/day, preferably from about 10-100 ug/kg/day.

pPRL according to the present invention can be administered to the poultry in any acceptable manner including orally, by injection, using an implant, and the like. Oral administration includes administering the compound in specially developed pharmaceutical compositions suitable for intestinal administration. These compositions prevent degradation of the protein by intestinal enzymes. An appropriate pharmaceutical composition is disclosed in U.S. Pat. No. 4,639,435, incorporated herein by reference. However, injections and implants are preferred, with injections being most preferred, because they permit precise control of the timing and dosage levels used for administration and avoid the loss of bioactivity when the protein is degraded by digestive enzymes.

pPRL according to the present invention is preferably administered parenterally. As used herein, parenteral administration means by intravenous, intramuscular, subcutaneous or intraperitoneal injection, or by subcutaneous implant.

When administered by injection, pPRL according to the present invention can be administered to the poultry in an injectable formulation containing any biocompatible and pPRL compatible carrier such as various vehicles, adjuvants, additives, and diluents. pPRL according to the present invention is added to the carrier in amounts sufficient to supply from about 1-500 mg to the poultry when injected. Preferably, pPRL according to the present invention is added to a polyvinylpyrrolidinone-NaCl vehicle in amounts sufficient to supply from about 10-100 ug/kg.

Aqueous vehicles such as water having no nonvolatile pyrogens, sterile water, and bacteriostatic water are also suitable to form injectable pPRL solutions. In addition to these forms of water, several other aqueous vehicles can be used. These include isotonic injection compositions that can be sterilized such as sodium chloride, Ringer's, dextrose, dextrose and sodium chloride, and lactated Ringer's. Addition of water-miscible solvents, such as methanol, ethanol, or propylene glycol generally increases solubility and stability of pPRL in these vehicles.

Nonaqueous vehicles such as cottonseed oil, sesame oil, or peanut oil and esters such as isopropyl myristate may also be used as solvent systems for pPRL compositions.

Additionally, various additives which enhance the stability, sterility, and isotonicity of the composition including antimicrobial preservatives, antioxidants, chelating agents, and buffers can be added. Any vehicle, diluent, or additive used would, however, have to be biocompatible and compatible with pPRL according to the present invention.

pPRL according to the present invention can be administered to the poultry in the form of a slow-release subcutaneous implant which is inserted beneath the skin of the bird. The implant can take the form of a pellet which slowly dissolves after being implanted in the bird or a biocompatible and bird compatible delivery module well known to those skilled in the art. Such well known dosage forms are designed such that the active ingredients are slowly released over a period of several days to several weeks. The implant is designed to deliver from about 1-500 ug/kg/day, preferably from about 10-100 ug/kg/day.

pPRL according to the present invention is used to promote growth in poultry such as chickens, quail, pheasants, ducks, turkeys, and the like.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

Effect of pPRL on Weight Gain and Feed Efficiency in Chickens

A growth trial was conducted using three-week old broiler cockerals to investigate the effect of pPRL on rate of weight gain, feed intake, and feed efficiency in chickens. The prolactin used in the trial was derived from pig pituitaries. The pPRL was dissolved in 10% polyvinylpyrrolidinone in 0.15N sodium chloride and administered by daily subcutaneous injections of either 0, 10, 50, or 100 micrograms of pPRL per kg of body weight per bird per day over a three week period. The birds were housed four to a cage in batteries, and started on test when 21 days old. Thirty-two cages and four treatments were used for a total of eight cages (32 birds) per treatment. Feed was of a mash type consisting of a corn-soybean meal base with added vitamins and minerals to approximate National Research Council nutritional recommendations for the type and age of chickens used in the experiment. Feed consumption, weight gain and mortality were measured during the experiment. The results are shown in Table 1 and FIG. 1.

Referring to FIG. 1, the data show a linear improvement in feed efficiency. As dose of pPRL is increased, feed efficiency is increased. The birds administered 100 micrograms per kg of body weight were 3% more efficient than those receiving an unmedicated placebo. Likewise, referring to Table 1, birds receiving 100 micrograms per kg of body weight gained weight 2% faster than those receiving an unmedicated placebo.

Obviously many modifications and variations of the present invention are possible in light of the above teachings. It is therefore to be understood that within the scope of the appended claims the invention may be practiced otherwise than as specifically described.

TABLE 1

| Item | pPRL, ug/kg of body weight/day | | | | SEM* |
|---|---|---|---|---|---|
| | 0 | 10 | 50 | 100 | |
| No. of Observations | 8 | 8 | 8 | 8 | |
| Avg. Daily Gain, g. | 60.4 | 59.6 | 60.3 | 61.6 | 0.88 |
| Avg. Daily Feed Int., g | 136.2 | 136.0 | 135.7 | 134.6 | 1.57 |
| Feed Eff. (Gain/Feed) | 0.444 | 0.438 | 0.445 | 0.458 | 0.0061 |

*Standard error of the mean.

What is claimed is:

1. A method for promoting growth in poultry, comprising:
   administering a growth promoting amount of porcine prolactin (pPRL) to the poultry.

2. The method of claim 1 wherein the porcine prolactin is administered to the poultry in amounts of from about 1-500 ug/kg/day.

3. The method of claim 2 wherein the porcine prolactin is administered to the poultry in amounts of from about 10-100 ug/kg/day.

4. The method of claim 1 wherein the porcine prolactin is administered parenterally.

5. The method of claim 4 wherein the porcine prolactin is administered using an implant, the implant further comprising:
   a biocompatible and porcine prolactin compatible implant material; and
   a growth promoting amount of the porcine prolactin.

6. The method of claim 3 wherein the porcine prolactin is administered in an injectable formulation, the injectable formulation further comprising:

a biocompatible and porcine prolactin compatible carrier; and a growth promoting amount of the porcine prolactin.

7. The method of claim 6 wherein the carrier is a polyvinylpyrrolidinone-NaCl vehicle.

8. The method of claim 1 wherein the porcine prolactin is administered orally.

9. The method of claim 1 wherein the porcine prolactin is a recombinant porcine prolactin.

10. The method of claim 1 wherein the poultry is selected from the group consisting of chickens, quail, pheasants, ducks, and turkeys.

11. The method of claim 1 wherein the poultry is chickens.

* * * * *

UNITED STATES PATENT AND TRADEMARK OFFICE
CERTIFICATE OF CORRECTION

PATENT NO. : 5,017,560

DATED : May 21, 1991

INVENTOR(S) : C.D. Baldwin, B.R. Shricker & R.E. Ivy

It is certified that error appears in the above-identified patent and that said Letters Patent is hereby corrected as shown below:

Column 1, line 49, "FRL" should read --PRL--.

Signed and Sealed this

Eighth Day of September, 1992

Attest:

DOUGLAS B. COMER

*Attesting Officer*  *Acting Commissioner of Patents and Trademarks*